United States Patent [19]

Larsson

[11] Patent Number: 5,049,126
[45] Date of Patent: Sep. 17, 1991

[54] BREAST PUMP WITH NIPPLE STIMULATING INSERT

[75] Inventor: Karl O. A. H. Larsson, Zug, Switzerland

[73] Assignee: ISG/AG, Baar, Switzerland

[21] Appl. No.: 480,879

[22] Filed: Feb. 16, 1990

[51] Int. Cl.$^5$ .............................................. A61M 1/06
[52] U.S. Cl. ...................................... 604/74; 604/75
[58] Field of Search ...................... 604/27, 35, 36, 37, 604/38, 73, 74, 75, 132, 133, 140, 141

[56] References Cited

U.S. PATENT DOCUMENTS

| 956,325 | 4/1910 | Fey . | |
| 975,047 | 11/1910 | Klein et al. . | |
| 1,156,202 | 10/1915 | Barrett . | |
| 1,184,631 | 5/1916 | De Leon . | |
| 1,460,927 | 7/1923 | Thompson et al. . | |
| 1,644,257 | 10/1927 | Lasker . | |
| 1,670,610 | 5/1928 | Colby . | |
| 1,847,656 | 3/1932 | Kratz . | |
| 2,000,710 | 5/1935 | Miller | 128/300 |
| 2,060,063 | 11/1936 | Frimand | 230/170 |
| 2,222,811 | 11/1940 | Dinesen | 230/190 |
| 2,419,795 | 4/1947 | Saunders | 128/297 |
| 2,542,505 | 2/1951 | Gascoigne | 128/281 |
| 3,165,584 | 4/1985 | Turner . | |
| 3,233,607 | 2/1966 | Bolie | 128/64 |
| 3,382,867 | 5/1968 | Reaves | 128/38 |
| 3,587,567 | 6/1971 | Schiff | 128/24.5 |
| 3,738,363 | 6/1973 | Lunas et al. | 128/281 |
| 3,782,385 | 1/1974 | Loyd | 128/281 |
| 3,822,703 | 7/1974 | Davisson | 128/281 |
| 3,911,920 | 10/1975 | Susinn | 128/281 |
| 3,977,405 | 8/1986 | Yanase | 128/281 |
| 4,249,481 | 2/1981 | Adams | 119/14.02 |
| 4,263,612 | 4/1981 | Gibson et al. | 358/31 |
| 4,311,141 | 1/1982 | Diamond | 128/281 |
| 4,323,067 | 4/1982 | Adams | 128/281 |
| 4,573,969 | 3/1986 | Schlensag et al. | 604/74 |
| 4,583,970 | 4/1986 | Kirchner | 604/74 |
| 4,673,388 | 6/1987 | Schlensog et al. | 604/74 |
| 4,680,028 | 7/1987 | Stuart | 604/74 |
| 4,759,747 | 7/1988 | Aida et al. | 604/74 |
| 4,794,915 | 1/1989 | Larsson | 128/64 |
| 4,799,922 | 1/1989 | Beer | 604/74 |
| 4,857,051 | 8/1989 | Larsson | 604/74 |
| 5,322,236 | 1/1895 | Hardesty . | |
| 6,840,078 | 10/1901 | Martin . | |

FOREIGN PATENT DOCUMENTS

| 2451953 | 5/1976 | Fed. Rep. of Germany . |
| 2807646 | 8/1978 | Fed. Rep. of Germany . |
| 251810 | 11/1947 | Switzerland . |
| 2995 | of 1911 | United Kingdom . |
| 660283 | 11/1950 | United Kingdom . |
| 762701 | 12/1956 | United Kingdom . |
| 271857 | 4/1977 | United Kingdom . |

OTHER PUBLICATIONS

Ruth A. Lawrence, M. D., Breastfeeding, Apr. 16, 1986, pp. 467–469.

Primary Examiner—Stephen C. Pellegrino
Assistant Examiner—Glenn K. Dawson
Attorney, Agent, or Firm—Willian Brinks Olds Hofer Gilson & Lione

[57] ABSTRACT

A breast milk pump with a hood insert for mechanically stimulating the nipples of a lactating woman. The insert has a nipple frame with openings that are covered by a flexible membrane. The membrane is drawn into the frame to gently massage the nipple area under action by a suction pump for the enhanced expression of milk.

7 Claims, 1 Drawing Sheet

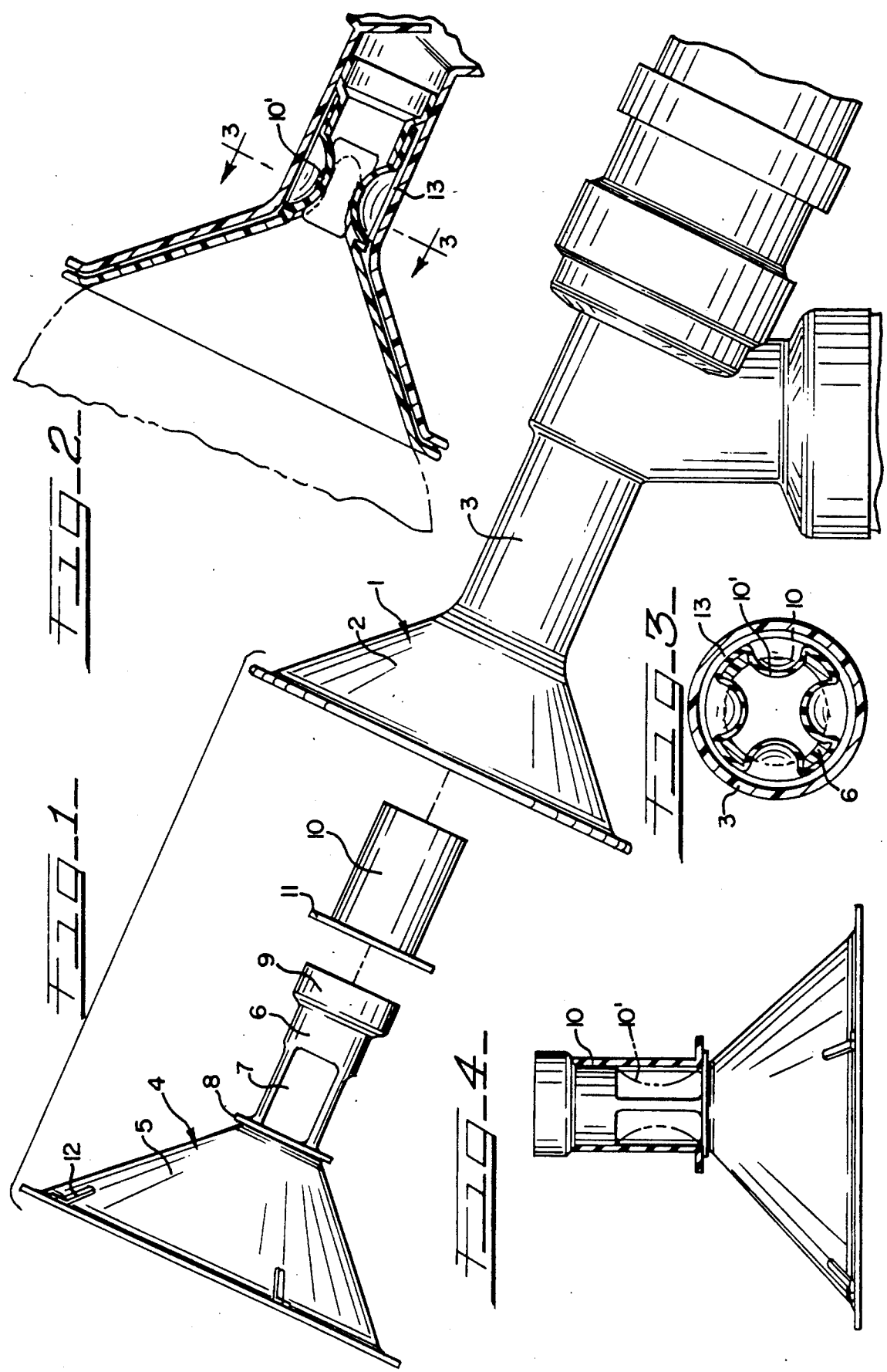

BREAST PUMP WITH NIPPLE STIMULATING INSERT

FIELD OF THE INVENTION

The present invention generally relates to breast pumps, and more particularly to an insert adapted to fit in a breast pump hood.

BACKGROUND OF THE INVENTION

Breast pumps are well known, and are generally comprised of a hood that fits over the breast, a vacuum pump connected to the hood for generating an intermittent vacuum (or negative pressure) within the hood, and a receptacle for expressed milk. The intermittent suction action of the vacuum pump serves to pull on the breast and nipple and thereby extract milk in an action reminiscent of suckling. The milk so extracted typically flows from the hood into a collection container for storage and later use. A breast pump of the foregoing type is shown in Larsson, U.S. Pat. No. 4,857,051, the disclosure of which is incorporated herein by reference.

Also disclosed in U.S. Pat. No. 4,857,051 is a rigid insert designed to decrease the cross-sectional area of the hood for use of the breast pump with smaller breasts. Soft inserts in breast pumps are also known in the art, as disclosed by U.S. Pat. No. 4,799,922. A drawback of many soft inserts is their tendency to pinch the nipple as the insert contracts under vacuum, causing discomfort and irritation.

A light stroking or squeezing of the sides of the nipple during lactation, however, enhances the expression of milk. Such action is more akin of the suckling of an infant.

SUMMARY OF THE INVENTION

A principal objective of the present invention is to provide a breast pump with an insert which creates a more realistic simulation of a suckling infant by having the insert gently squeeze and massage the nipple during lactation.

This objective is met in the present invention which utilizes a breast pump having a hood body for placement over a breast. The hood body has a funnel-shaped portion applied over the breast with an outlet through which the nipple extends, and a tube extending downstream from the outlet.

The inventive insert is adapted to be received within the hood body, and has a funnel-shaped portion generally conforming to the shape of the hood funnel-shaped portion, with an insert outlet through which the nipple also extends. A tubular frame extends downstream from the insert outlet within which the nipple is received. The frame has at least one elongated opening therein located at a point overlying the nipple. A flexible member, such as an elastic membrane, overlies the opening.

Upon the generation of a reduced pressure within the hood body and insert by the action of a vacuum pump, the membrane is drawn within the frame through the frame opening. The membrane thereby gently squeezes and massages the nipple for the enhanced expression of milk.

In a presently preferred embodiment, the foregoing frame has a plurality of longitudinally extending elongated openings evenly spaced about the frame, with each opening located at a point overlying the nipple. A flexible sleeve membrane fits over the outside of the frame and overlies the openings.

This tubular frame design permits the membrane to collapse only in the center portion of the openings, thus stroking and not pinching the nipple on its sides, and preventing irritation of the nipple tip. The flexible membrane sleeve is also easily removed for cleaning or replacement.

The insert is further designed to fit within an existing breast pump. No modification of the breast pump is therefore required.

The foregoing objects and advantages of the present invention will be further understood upon consideration of the following detailed description of the invention taken in conjunction with the following drawings, in which:

BRIEF DESCRIPTION OF THE DRAWINGS

FIG. 1 is an exploded elevational view of a breast hood with insert and flexible membrane sleeve made in accordance with the present invention;

FIG. 2 is a sectional view of the breast hood of FIG. 1 applied to a breast;

FIG. 3 is a sectional view taken along line 3—3 of FIG. 2; and

FIG. 4 is an elevational view, partly in section, of the insert of FIG. 1 assembled with the flexible membrane.

DETAILED DESCRIPTION OF AN EMBODIMENT OF THE INVENTION

The breast pump apparatus shown in FIGS. 1-4 has a hood body 1 with a funnel shaped portion 2 and a tubular portion 3. The breast pump depicted is substantially the same as that shown in U.S. Pat. No. 4,857,051, and reference can be made to that patent for specific details of the breast pump and its operation.

An insert 4 having funnel portion 5 and a nipple receptor tube or frame 6 is adapted to fit in the hood body 1. The frame 6 has formed on its lateral surface a plurality of elongated openings 7. As shown in FIG. 3, the preferred embodiment provides for four longitudinally extending openings spaced evenly about the frame 6.

A flexible membrane made of a thinly drawn latex sleeve 10 fits over the frame 6 covering the openings 7. Silicone could also be used for the membrane material. The preferred embodiment of the sleeve 10 has a rim 11 thereon which abuts a lip 8 formed at then arrow end of the funnel portion 5 of the insert 4. The rim 11 can be grasped to facilitate removal of the flexible membrane sleeve 10. The other end of the flexible membrane sleeve abuts a widened portion 9 of the frame. The outside of the widened portion 9 forms a press-fit (interference) seal with the interior wall of the tubular extension 3 of the hood body 1 (which has a slightly inward taper downstream).

Stand-off members 12 permit air to enter into an air gap 13 between the interior of the tubular extension 3 of the hood body 1 and the exterior of the frame 6 with its flexible membrane sleeve 10. This embodiment has four evenly spaced stand off members 12 formed adjacent the forward edge of the funnel portion 5 of the insert 4.

In use, the insert 4 is placed within the hood body 1, and the breast pump is lightly pressed over the breast while operating the pump. A negative pressure is intermittently generated within the insert 4. The negative pressure causes the flexible membrane 10 to be drawn through the openings 7 into frame interior. The flexible membrane deforms to approximately the form 10', shown in solid line in FIGS. 2 and 3, and in phantom in FIG. 4. In the process, the sides of the nipple are gently intermittently squeezed or stroked, and thereby stimulated for enhanced milk production. As shown in FIG. 2, the opened cylindrical design of the frame 6, combined with the flexible membrane sleeve 10, permits the membrane to collapse in the middle portion of the openings 7, thereby generally avoiding irritation to the tip of the nipple. The preferred embodiment has an insert frame about 1½ inches long with an internal diameter of approximately ¾ of an inch. The openings in the frame are approximately 7/16 inch wide by ¾ inch long.

While a flexible membrane sleeve 10 is considered most advantageous, it is also conceivable that a flexible member could be separately located over each opening (as by gluing thereover). The openings 7 could also be of a different shape from that described herein.

Thus, while the invention has been described with reference to a certain embodiment, those skilled in this art will recognize modifications of structure, arrangement, composition and the like that can be made with respect to the present invention, yet still fall within the scope of the invention as hereafter claimed.

What is claimed is:

1. A breast pump for mother's milk comprising:
   a hood body for placement over a breast, said hood body having a funnel-shaped portion applied over the breast with an outlet through which a nipple extends, and a tubular portion extending downstream from said outlet,
   means for producing an intermittent vacuum in said hood body,
   means for collecting expressed milk,
   an insert adapted to be received within said hood body in an air-sealing engagement therewith, said insert having a funnel-shaped portion generally conforming to the shape of said hood funnel-shaped portion with an insert outlet through which the nipple extends, and a tubular frame extending downstream from said insert outlet within which the nipple is received, said tubular frame having at least one opening therein located at a point overlying the nipple extending within said tubular frame, means for providing ambient air to an exterior of said tubular frame, and a flexible member overlying said opening which, upon the generation of a reduced pressure within said insert by the action of said means for producing an intermittent vacuum, gently squeezes and massages the nipple for an enhanced expression of milk.

2. The apparatus of claim 1 wherein said flexible member is a sleeve membrane which slides over said tubular frame exterior to overlie and cover said at least one opening of said tubular frame.

3. The apparatus of claim 1 wherein said means for providing ambient air to an exterior of said tubular frame comprises stand-off members spacing said insert funnel-shaped portion from said hood body funnel-shaped portion to form an air gap for admitting environmental air to said exterior of said tubular frame and wherein said tubular frame has a sealing portion which engages said hood body tubular portion to form an air seal therewith.

4. A breast pump for mother's milk comprising:
   a hood body for placement over a breast, said hood body having a funnel-shaped portion applied over the breast with an outlet through which a nipple extends, and a tube extending downstream from said outlet,
   means for producing an intermittent vacuum in said hood body,
   means for collecting expressed milk, and
   an insert received within said hood body, said insert having a funnel-shaped portion generally conforming to the shape of said hood funnel-shaped portion with an outlet through which the nipple extends, and a tubular frame extending downstream from said insert outlet within which the nipple is received,
   said tubular frame having a plurality of longitudinally extending elongated openings therein spaced about said tubular frame each located at a point overlying the nipple extending within said tubular frame, a flexible membrane sleeve received on said tubular frame overlying and covering said elongated openings,
   and stand-off members formed on said insert funnel-shaped portion spacing said insert funnel-shaped portion from said hood body funnel-shaped portion to form an air gap for admitting environmental air to an exterior surface of said flexible membrane sleeve, said tubular frame having a sealing portion which engages said hood body tube to form an air seal therewith,
   said flexible membrane sleeve, upon the generation of a reduced pressure within said hood body and insert by the action of said means for producing an intermittent vacuum, being pulled through said elongated openings to gently squeeze and message the nipple for an enhanced expression of milk.

5. The apparatus in claim 4 further comprising a finger-grippable rim formed on said flexible membrane sleeve.

6. The apparatus of claim 4 wherein said sealing portion comprises a widened portion on said tubular frame downstream from said elongated openings, said widened portion forming a press-fit seal with an interior surface of said hood body tube.

7. An insert for a breast pump having a hood body for placement over a human breast, with a main funnel portion within which the breast is received and a tubular extension extending in a downstream direction from said main funnel portion, wherein the insert comprises:
   a funnel-shaped portion adapted to be received in said hood main funnel portion and generally conforming to the shape of said hood main funnel portion, and a tubular frame adapted to be received within the hood tubular extension, said tubular frame having at least one enlarged opening formed therein at a point overlying a nipple received within said frame; and
   a flexible membrane covering said at least one opening of said frame, said flexible membrane under the action of a negative pressure within said insert, with a less negative pressure outside of said insert, extending through said at least one opening to squeeze and massage the nipple.

* * * * *

UNITED STATES PATENT AND TRADEMARK OFFICE
CERTIFICATE OF CORRECTION

PATENT NO. : 5,049,126
DATED : September 17, 1991
INVENTOR(S) : Karl O.A.H. Larsson It is certified that error appears in the above-identified patent and that said Letters Patent is hereby corrected as shown below:

Title page, under item [56]
   IN THE REFERENCES CITED
 delete "5,322,236" and
   substitute therefor --532,236--; and delete "6,840,078" and
   substitute therefor --684,078--.
On title page, item [56], delete "3,165,584" and substitute --316,584--.

Column 4, line 35,
   in claim 4, delete "message" and
   substitute therefor --massage--.

Signed and Sealed this

Thirtieth Day of March, 1993

*Attest:*

STEPHEN G. KUNIN

*Attesting Officer*     *Acting Commissioner of Patents and Trademarks*